United States Patent
Bae et al.

(10) Patent No.: US 6,703,049 B2
(45) Date of Patent: Mar. 9, 2004

(54) ANGIOGENESIS INHIBITOR

(75) Inventors: Il Ju Bae, Seoul (KR); Kang Moon Seo, Seoul (KR); Chang Hun Rhee, Seoul (KR)

(73) Assignee: Il Ju Bae, Seoul (KR)

(*) Notice: Subject to any disclaimer, the term of this patent is extended or adjusted under 35 U.S.C. 154(b) by 0 days.

(21) Appl. No.: 09/824,879

(22) Filed: Apr. 4, 2001

(65) Prior Publication Data

US 2002/0001630 A1 Jan. 3, 2002

(30) Foreign Application Priority Data

Jun. 29, 2000 (KR) ......................... 2000-36452

(51) Int. Cl.⁷ ............................... A61K 33/36
(52) U.S. Cl. .................. 424/623; 514/824; 514/825; 514/863; 514/866; 514/894; 514/912; 514/914; 514/925; 514/934
(58) Field of Search .................. 424/623; 514/824, 514/825, 863, 894, 912, 925, 934, 866, 914

(56) References Cited

U.S. PATENT DOCUMENTS 6,309,672 B1 * 10/2001 Bae et al. ................ 424/623
6,589,567 B2 *  7/2003 Bae et al. ................ 424/623

FOREIGN PATENT DOCUMENTS

| EP | 0955052 A1 | 11/1999 |
| FR | 2 782 010 | 2/2000 |
| FR | 2 786 103 | 5/2000 |
| WO | WO 99/24029 | 5/1999 |

OTHER PUBLICATIONS

Soignet, S. L. et al., "Complete remission after treatment of acute promyelocytic leukemia with arsenic trioxide," The New England Journal of Medicine, Nov. 5, 1998, vol. 339(19), pp. 1341–1348.*

World Health Organization Health and Safety Guide No. 70, Geneva, 1992, pp. 7–11.*

Chemical Abstracts 133:183042, abstracting CN 1231922 (1999).*

Kirk–Othmer Encyclopedia of Chemical Technology, John Wiley & Sons, New York, 4$^{th}$ edition, 1992, vol. 3, pp. 637–638.*

XP–008013830, G.J. Roboz, et al., "Arsenic Trioxide (As2O3) Exerts Its Anti–Leukemic Effect by Inhibiting Angiogenesis," Hematology–Oncology Div., Cornell Medical College, and Sloan–Kettering Cancer Center, NY, NY, USA, PD: Nov. 15, 1998, p. 598A.

XP–002231646, Weast, R.C., "CRC Handbook of Chemistry and Physics," CRC–Handbook of Chemistry and Physics. Ready Reference Book of Chemical and Physical Data, Boca Raton, CRC Press, U.S., vol. Ed. 69, p. B–73, line 57–line 58 (date unknown).

XP–008013801, Robert J. Griffin, et al., "Arsenic Trioxide Reduces Tumor Blood Flow, Inhibits Endothelial Cell Growth and Selectively Kills Hypoxic Cells," *Proceedings of the American Association for Cancer Research Annual Meeting*, PD: Mar. 2000, No. 41, p. 650.

XP–008013833, "Arsenic Trioxide Induces Apoptosis of Oesophageal Carcinoma in vitro," *International Journal of Molecular Medicine*, PD: Jul. 1999, pp. 33–37.

* cited by examiner

*Primary Examiner*—John Pak
(74) *Attorney, Agent, or Firm*—Pillsbury Winthrop LLP; Intellectual Property Group

(57) ABSTRACT

The present invention relates to a novel angiogenesis inhibitor, more particularly, arsenolite (solid $As_4O_6$) and composition containing the same. The arsenolite of the present invention inhibits endothelial cell proliferation and tube formation so that it can be used for medication of various angiogenic diseases.

8 Claims, 4 Drawing Sheets

ANGIOGENESIS INHIBITOR

BACKGROUND OF THE INVENTION

1. Field of the Invention

The present invention relates to the use of solid arsenolite ($As_4O_6$), which is an angiogenesis inhibitor, and pharmaceutical composition containing the same. In particular, the present invention relates to newly discovered applications of $As_4O_6$, previously known as 'Chonjisan®', as treatment for angiogenesis and other associated diseases.

2. Description of the Background Art

Angiogenesis, the process of new vessel formation by the endothelial cells, is critical for the growth of tumors (Folkman J. Watson K, Ingber D, Hnahan D, Induction of angiogenesis during the transition from hyperplasia to neoplasia, Nature May 4, 1989; 339(6219); 58–61). And, its dominant feature is more obvious in many angiogenic disease like diabetic retinopathy, arthritis, hemangiomas and psoriasisis (Klagsbrun M & Folkman J in Peptide Growth Factors and Their Receptors II (eds Sporn M. B & Roberts, A. B.) 549–586 (Spring, Berlin, 1990)).

Neovascularization or invasion of vessels is usually observed in the corneas of patients suffering from Stevens-Johnson syndrome and similar diseases; ocular pemphigoid and similar diseases; corneal chemical injuries due to toxic chemicals i.e., alkalin, acid, detergent, or various kinds of solvents and volatile gases; trachoma; virus infection; phlyctenula keratitis; and patients who received corneal transplant, and patients who use contact lenses for long periods. Aqueous chamber, lenses or vitreous are originally transparent without vessel and if neovascularization occurs in these tissues, severe visual loss results in difficulty in every day life. Thus, a number of medicinal researches have been done to inhibit neovascularization.

Typically known angiogenesis inhibitors include protamine application (Taylor, S. et al., Nature, 297, 307, 1982), combination of heparine and cortizon (Folkman, J. et al., Science, 221, 71, 1983), predonisolone acetate (Robin, J. B., Arch, Opthalmol., 103, 284, 1985), sulfonated polysaccharide (Japanese laid-open No. 63-119500), Herbimycin A (Japanese patent laid-open No. 63-295509), Fumagillin (Japanese patent laid-open No. 1-279828) and interferon beta (U.S. Pat. No. 5,948,403). However, most of these are unsatisfactory because of insufficient activity, and especially, their adverse side effect on a human body has been a serious concern.

Arsenic is a well-known potent environmental carcinogen to cause skin and lung cancers. However, there have been used for treating psoriasis, syphilis, and rheumatism in the traditional oriental medicine. It was not until in 1970's that Chinese discovered that arsenic trioxide ($As_2O_3$) remarkably cured acute promyelocytic leukemia (APL). Now, many researches are actively in process all over the world including the United States in connection with arsenic compounds' functional groups and applications thereof (Zhang T D: Treatment of acute granulocytic leukemia with "Ai Ling No. 1"—Clinical analysis and experimental research. Chin J Integrated Chin West Med 4:19, 1984) (Li Y S, Zhang T D, Li C H W, Zhao X L, Wei Z H R, Tan W, Li R L, Mao Y Y: Traditional Chinese and Western Medicine in the treatment of 27 patients with malignant lymphoma. Chin J Oncol 10:61, 1988) (Sun H D, Ma L, Hu X C, Zhang T D: Ai-Lin I treated 32 cases of acute promyelocytic leukemia. Chin J Integrated Chin West Med 12:170, 1992, Blood May 1, 1997; 89(9): 3354–60 Use of arsenic trioxide ($As_2O_3$) in the treatment of acute promyelocytic leukemia (APL): II. Clinical efficacy and pharmacokinetics in relapsed patients. Shen Z X, Chen G Q, Ni J H, Li X S, Xiong S M, Qiu Q Y, Zhu J, Tang W, Sun G L, Yang K Q, Chen Y, Zhou L, Fang Z W, Wang Y T, Ma J, Zhang T D, Chen S J, Chen Z, Wang Z Y).

In western countries, arsenic compounds were once used for treating syphilis, but now Melarsoprol, an organic arsenical used for treating trypanosomiasis, is the only arsenic compound in use. In vitro studies revealed that arsenic trioxide and Melarsoprol, is cytotoxic not only to APL cells but also to other types of leukemia cells by induction of apoptosis through the down regulation of Bcl-2 protein and/or activation of caspases (Blood Sep. 1, 1998;92 (5): 1497–504 Arsenic trioxide and melarsoprol induce programmed cell death in myeloid leukemia cell lines and function in PML and PML-RAR alpha independent manner. Wang Z G, Rivi R, Delva L, Konig A Scheinberg D A, Gambacorti-Passerini C, Gabrilove J L, Warrell R P Jr., Pandolfi P P, Blood Aug. 1, 1996;88 (3): 1052–61 In vitro studies on cellular and molecular mechanisms of arsenic trioxide ($As_2O_3$) in the treatment of acute promyelocytic leukemia: $As_2O_3$ induces NB4 cell apoptosis with down regulation of Bcl-2 expression and modulation of PML-RAR alpha/PML proteins. Chen G Q, Zhu J, Shi X G, Ni J H, Zhong H J, Si G Y, Jin X L, Tang W, Li X S, Xong S M, Shen Z X, Sun G L, Ma J, Zhang P, Zhang T D, Gazin C, Naoe T, Chen S J, Wang Z Y, Chen Z, Blood May 1, 1997; 89(9):3345–53 Use of arsenic trioxide ($As_2O_3$) in the treatment of acute promyelocytic leukemia (APL): I. $As_2O_3$ exerts dose-dependent dual effects on APL cells. Chen G Q, Shi X G, Tang W, Xiong S M, Zhu J, Cai X, Han Z G, Ni JH, Shi G Y, Jia P M, Liu M M, He K L, Niu C, Ma J, Zhang P, Zhang T D, Paul P, Naoe T, Kitamura K, Miller W, Waxam S, Wang Z Y, de The H, Chen S J, Chen Z, Br J Haematol September 1998; 102(4):1055–60 Arsenic induces apoptosis in B-cell leukaemic cell lines in vitro: activation of caspases and down-regulation of Bcl-2 protein. Akao Y, Mizoguchi H, Kojima S, Naoe T, Ohishi N, Yagi K, Blood Jul. 15, 1997;90(2): 562–70, Comparative activity of melarsoprol and arsenic trioxide in chronic B-cell leukemia lines., Konig A, Wrazel L, Warrell R P Jr., Rivi R, Pandolfi P P, Jakubowski A, Gabrilove J L).

Tetraarsenic oxide (solid $As_4O_6$) provides the starting material for arsenic trioxide and most other arsenic compounds, and is also utilized in pesticides and serves as a decolourizer in the manufacture of glass and as a preservative for hides. Therefore, the arsenolite was believed to be a toxic, carcinogenic chemical substance just like arsenic trioxide, and only its molecular structure has been the chemist's main concern (Becker K. A., Plieth K., and Stranski I. N. The polymorphic modifications of arsenic trioxide. Prog. Inorg. Chem. 4, 1–72 (1962), Pupp C, Lao R. C., Murray J. J., pottie R. F., Equilibrium vapor concentrations of some polycyclic aromatic hydrocarbons, $As_4O_6$ and $SeO_2$ and the collection efficiencies of these air pollutants. Atmospheric Environment Vol. 8, pp 915–925, 1974, Grzechnik A. Compressibility and vibrational modes in solid $As_4O_6$ Journal of Solid State Chemistry, 144 (2):416–422, May 1999).

In the meantime, the inventor discovered that $As_4O_6$, which was obtained from natural arsenic bearing ore, could be used as an anti-cancer agent, so he filed a patent application no. 1998-16486 with Korean Industrial Property Office, and in 1999, he was granted a patent on this same invention from Japanese Patent Office (Japanese Patent No. 3007627).

It was reported that arsenic trioxide, when taken through oral administration, caused serious side effect on gastrointestinal and liver (Shen Z X, Chen G Q, Ni J H, Li X S, Xiong S M, Qiu Q Y, Zhu J, Tang W, Sun G L, Yang K Q, Chen Y, Zhou L, Fang Z W, Wang Y T, Ma J, Zhang P, Zhang T D, Chen S J, Chen Z, Wang Z Y Use of arsenic trioxide ($As_2O_3$) in the treatment of acute promyelocytic leukemia (APL): II. Clinical efficacy and pharmacokinetics in relapsed patients. Blood May 1, 1997; 89(9): 3354–60). However, according to the inventor's experiment, when oral administration of 100 mg/kg of arsenolite had been done for 28 days to the Sprague Dawley rat weighting around 200 g, only minor histological alterations was observed in kidney and no side affect on gastrointestinal and liver. Further, if 10 mg/kg and 1 mg/kg were applied, none of side effect was observed.

SUMMARY OF THE INVENTION

Accordingly, it is an object of the present invention to provide a novel angiogenesis inhibitor, arsenolite.

Another object of the present invention is to provide pharmaceutical compositions comprising the angiogenesis inhibitor described above.

DETAILED DESCRIPTION OF THE INVENTION

Figure 1:
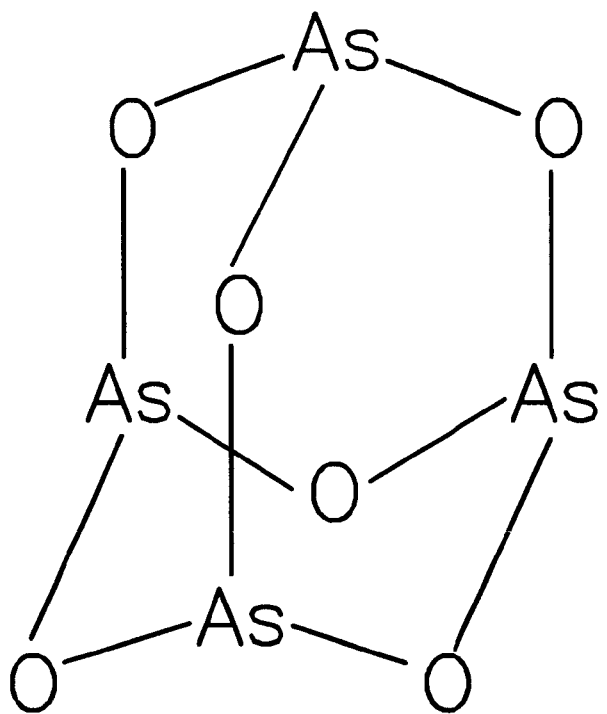
FIG. 1 is a three dimensional structure of angiogenesis inhibitor of the present invention.

In order to achieve the objects described above, the inventor performed in vitro and in vivo experiment using arsenolite, of which structure is shown in FIG. 1, and discovered that arsenolite inhibited chemotaxis of capillary endothelial cells and new vessel formation induced by basic Fibroblast Growth Factor (bFGF).

Arsenolite of the invention has been known as 'Chonjisan®', and preparation method thereof was already publicized through Korean patent number 1998-16486 by the same inventor. According to the method, pure solid arsenolite is prepared by series of heat processes using natural arsenic bearing ore or arsenic reagent. Since the method can be referred to the patent aforementioned, it won't be detailed here. It would be enough to mention that other preparation methods can also be employed as long as the resultant arsenolite has the same structure as shown in FIG. 1.

When approximately 50 mg/kg/day of angiogenesis inhibitor of the present invention was orally administered to a rat, it was proved that corneal neovascularization stimulated by bFGF was noticeably suppressed. In case a human is involved, dose of the angiogenesis inhibitor can be adjusted depending on a patient's disease, age, sex and health.

Angiogenesis inhibitor of the present invention can be used separately or combined with other angiogenesis inhibitors. Excipient, disintegrator, flavor, glidants and other pharmaceutically allowed supplements are usually combined with arsenolite, and these are applied through oral or parenteral administration. Here, the formulation takes one of powder, tablet or liquid forms.

Furthermore, angiogenesis inhibitor of the present invention is used separately or combined with other medication for treatment of many kinds of diseases that are associated with angiogenesis mechanism, for example, cancers, diabetic retinitis, rheumatoid arthritis, hemangioma and psoriasis.

The present invention will now be described in more detail by referring to the examples below, which are not intended to be limiting.

EXAMPLE 1

Inhibition of Endothelial Cell Proliferation

The following experiments are done for investigating whether or not arsenolite inhibits bovine capillary endothelial (BCE) cell proliferation.

1) Animals, reagents and cells

Male Sprague-Dawley rats weighing 200 g were used as an experimental animal. Arsenolite (solid $As_4O_6$) was dissolved in water until it becomes a 1 mM of stock solution, and kept at the room temperature. Bovine capillary endothelial (BCE) cells were provided by Dr. Tae-Hee Lee (Lee, T. H., Rhim, T., and Kim, S. S. (1998). Prothromb inkringle-2 domain has a growth inhibitory activity against basic fibroblast growth factor-stimulated capillary endothelial cells. J. Biol. Chem 273, 28805–28812). BCE cells were preserved in Dulbecco's modified Eagle's medium (DMEM) supplemented with 10% heat-inactivated bovine calf serum (BCS; Hyclone Laboratories, Logan, Utah) L-glutamine (2 mM), penicillin (110 units/ml), streptomycin (100 $\mu$g/ml) and 1.5 ng/ml recombinant human basic fibroblast growth factor (bFGF; R&D Systems, Minneapolis, Minn.). Then, the cells were incubated at 37° C. under 10% $CO_2$ condition. The cells between 10–15 passages were employed in this experiment.

2) Endothelial Cell Proliferation Assay

Endothelial proliferation assay was performed as described by Cao et al. (Cao, Y., A., An, S. S. A., Ji, R. W., Davodson, D., Cao, Y., and Llinas, M. (1997) Kringle 5 of plasminogen is a novel inhibitor for endothelial cell growth. J. Biol. Chem. 271, 22924–22928). Cells growing in gelatin-coated plates were dispersed in 0.05% trypsin solution and resuspended with DMEM containing 10% BCS. Approximately 12,500 cells were added to each well of gelatinized 24-well plates and incubated at 37° C. under 10% $CO_2$ for 24 hours. The media were replaced with 0.25 ml of fresh DMEM containing 5% BCS, and samples were added to each well. After 30 min of incubation, media were added to a final volume of 0.5 ml of DMEM containing 5% BCS and bFGF at 3 ng/ml. After 72 hours of incubation, the cells were trypsinized and counted using a hemocytometer. Each condition was prepared in triplicate, and the experiment were carried out three times.

Figure 2:
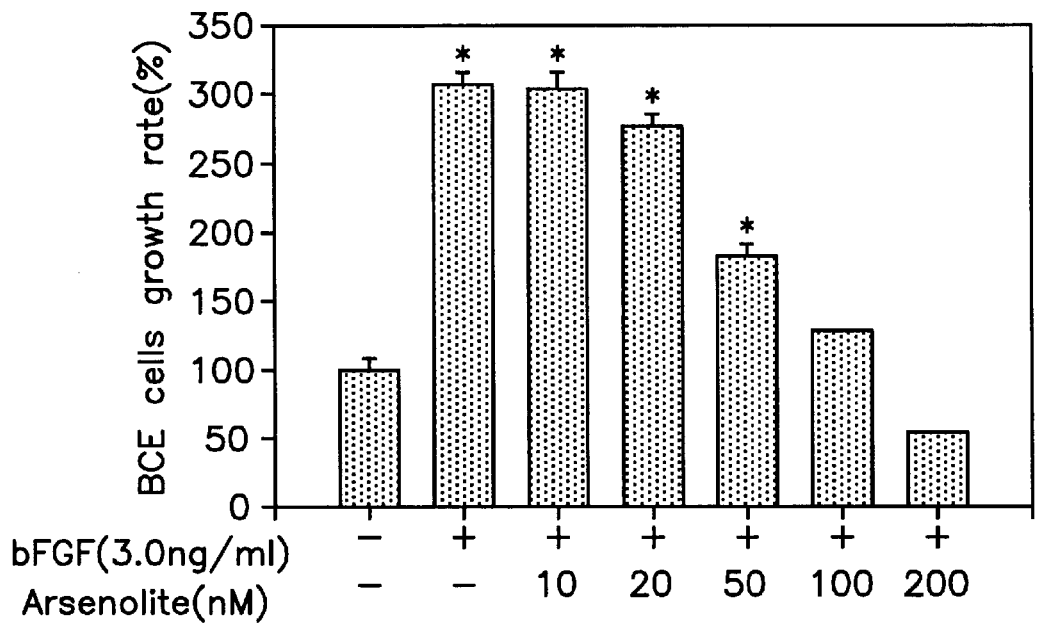
FIG. 2 is a graph showing inhibition of BCE cell proliferation by treatment with arsenolite of the present invention.

In particular, arsenolite at concentrations of 10 to 200 nM (10 nM, 20 nM, 50 nM, 100 nM and 200 nM) were assayed on BCE cells in the presence of 3 ng/ml bFGF. FIG. 2 shows data obtained from cells with bFGF and control cells without bFGF stimulation for comparison. In result, inhibition of BCE cell proliferation by arsenolite was the greatest in 100 mM, showing that the inhibition effect depends on a dose ($IC_{50}$=99 nM). No distinct cell morphological changes in associated with apoptotic endothelial cells including detachment, rounding, and fragmentation were detected after a 3-day incubation.

EXAMPLE 2

Effect of Arsenolite on Endothelial Cell's Invasiveness

An effect of arsenolite on the invasiveness of bovine capillary endothelial (BCE) was determined.
1) Animals and cells
The same animals and cells as in Example 1 were employed.
2) Effect of arsenolite on chemotaxis
Chemotaxis assays were performed using modified Boyden chambers, which is equipped with polycarbonate nucleopore membrane (Boyden Chamber, Corning, Coring, N.Y.) described in Journal (Veronique Rigot, Maxime Lehmann, Frederic andre, Noucha Daemi, Jacques Marvaldi and Jose Luis: Integrin ligation and PKC activation are required for migration of colon carcinoma cells. Journal of cell science 111, 3119–3129 (1998)). Pre-coated filters (6.5 mm in diameter, 8 μm pore-size, Matrigel 100 μg/cm$^2$) were re-hydrated with 250 μl of medium, and 1×10$^5$ cells in 200 μl medium with or without arsenolite (at concentrations of 10 nM, 20 nM, 50 nM, 100 nM and 200 nM) in triple respectively were seeded into the upper part of each chamber, whereas the lower compartment was filled with 200 μl of serum free DMEM supplemented with 0.1% BSA and with (positive control) or without (negative control) 10 ng/ml bFGF as a chemoattractant. After the cells were incubated at 37° C. for 72 hours, non-migrated cells on the upper surface of the filter were wiped with a cotton swab, and migrated cells on the lower surface of the filter were fixed and stained with 0.125% Cumassie Blue in a mixture of methanol: acetic acid: water at the ratio of 45:10:45 by volume. Chemotaxis was determined by counting cells in five microscopic fields per well, and the extent of migration is expressed as an average number of cells per each microscopic field.

Figure 3:
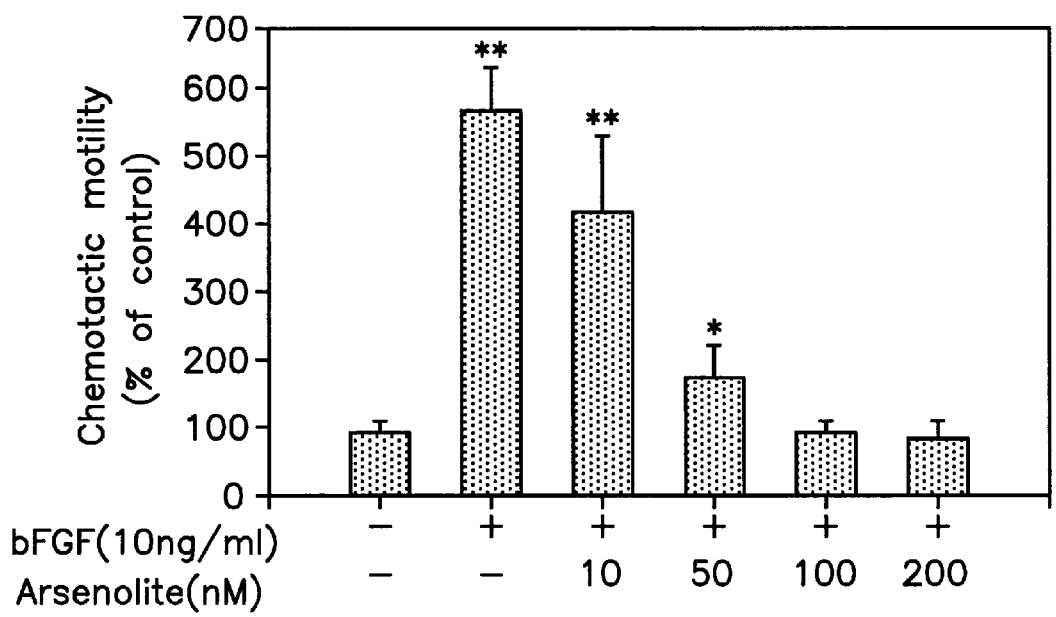
FIG. 3 is a graph showing effect of arsenolite on chemotaxix of BCE cells.

As shown in FIG. 3, the cells were severely invaded by bFGF treatment. However, this invasiveness was blocked by pretreatment with arsenolite as a concentration dependent manner. The inhibition reached as high as 83.4% at 100 nM where $IC_{50}$ is 48 nM. On the other hand, none of distinct cell morphological changes in associated with apoptotic endothelial cells including detachment, rounding, and fragmentation was observed.

EXAMPLE 3

Effect of Arsenolite on the Tube Formation of BCE Cells in 3-D Cultures

To investigate the effect of arsenolite on the maturation of angiogenesis, particularly, tubular structure formation of capillary endothelial cells, BCE cells were cultured using three dimensional cultures on the fibrin gel.
1) Animals and cells
The same animals and cells as in Example 1 were employed.
2) Tube Formation Assay
Fibrin gels were prepared by following a reported procedure (Bastaki M, Nelli E E, Dell'Era P, Rusnati M, Molinari-Tosatti M P, Parolini S, Auerbach R, Ruco L P, Possati L, Presta M, Basic fibrolast growth factor-induced angiogenic phenotype in mouse endothelium. A study of aortic and microvascular endothelial cell lines. Arterioscler Thromb Vasc Bio March 1997; 17(3): 454–64). Briefly, 2.5 mg/ml of fibrinogen (Calbiochem, San Diego, Calif.) was dissolved in DMEM and cultured BCE cells were added to a final concentration of 10$^5$ cells/ml, and clotting was then initiated by addition of thrombin (0.5 unit/ml). The mixture was immediately transferred into 24-well plates and allowed to form gel for 5 minutes at 37° C. Following get formation, 0.5 ml of medium with or without bFGF (10 ng/ml) and arsenolite (100 nM) per well were added. After 48 or 96 hours, tube formation was examined under inverted microscopy.

Figure 4:
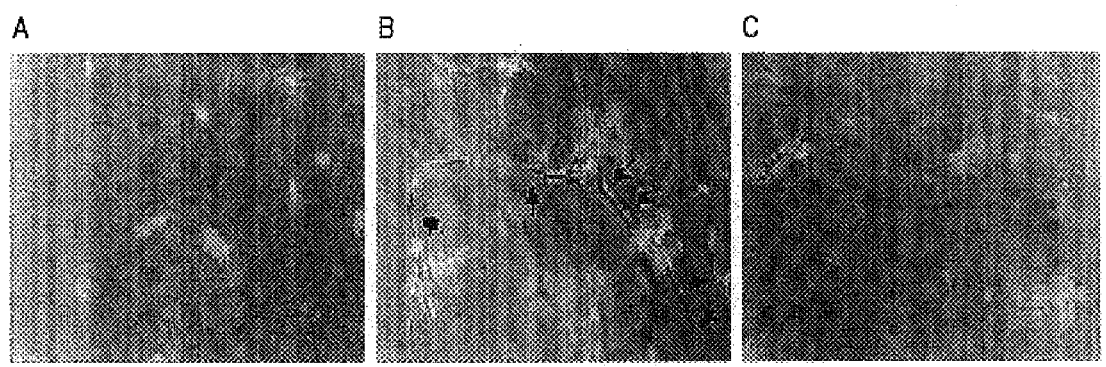
FIGS. 4(A) through 4(C) show inhibitory effect of arsenolite of the present invention on new vessel formation.

FIGS. 4A and 4B show that BCE cells on fibrin gel ungergo alignment into cords and maximum tube like structure formation was accomplished. FIG. 4C shows that generation of tubes by BCE cells was reduced by the arsenolite treatment. In conclusion, arsenolite inhibits the endothelial cell differentiation in 3D cultures.

EXAMPLE 4

Corneal Micropocket Angiogenesis Assay

To further investigate the antiangiogenic activity of arsenolite in vivo, the inhibitory effect of systematically administered arsenolite on bFGF-induced neovascularization was studied. The corneal micropocket assay was performed by slight modification of a reported procedure (Polverim P J, Bouck N P, Rastinejad F. Assay and purification of naturally occurring inhibitor of angiogenesis, Methods Enzymol. 1991; 198: 440–450). That is, rats were anesthetized with ketamine. A corneal pocket was made by inserting a cataract knife, with the pocket's base 1–1.5 mm from the limbus. Pellets were made by mixing 30 μl of saline containing 2 μg of recombinant bFGF (R&D Systems, Minneapolis, Minn. U.S.A.) with 300 μg of sucralfate (Sigma, St. Louis, Mo., U.S.A.); this suspension was added to 30 μl of 12% (wt/vol) poly (2-hydroxyethyl methacylate) (Sigma, St. Louis, Mo., U.S.A.) in ethanol. Aliquots of this mixture were then pined onto Teflon pegs and allowed to dry producing approximately 17 pellets so that each pellet contains approximately 100 ng of bFGF. A pellet was implanted into corneal micropockets of each eye of an anesthetized male Sprague Dawley rat, followed by a single topical application of erythromycin ointment on the surface of the cornea. The animals were fed daily from the day of implantation by gastric lavage with 50 mg/kg of arsenolite powder for the treatment group, and the same foods and water without arsenolite for the control group. The corneal neovascularization in both eyes of all animals were examined daily with a slit lamp and the angiogenic responses were evaluated on day 7. The area of conical neovascularization was determined by measuring with a reticule the vessel length (L) from the limbus and the number of clock hours (C) of limbus involved as previously reported (D'Amato R I, Loughnan M S, Flynn E, Foulkman J, Thalidomide is an inhibitor of angiogenesis. Proc Natl Acad Sci USA Apr. 26, 1994; 91(9):4082–5). A formula was used to determine the area of a circular band segment: $C/12 \times 3.1416[r^2-(rL)^2]$, where r=5 mm, the measured radius of rat cornea.

Figure 5:
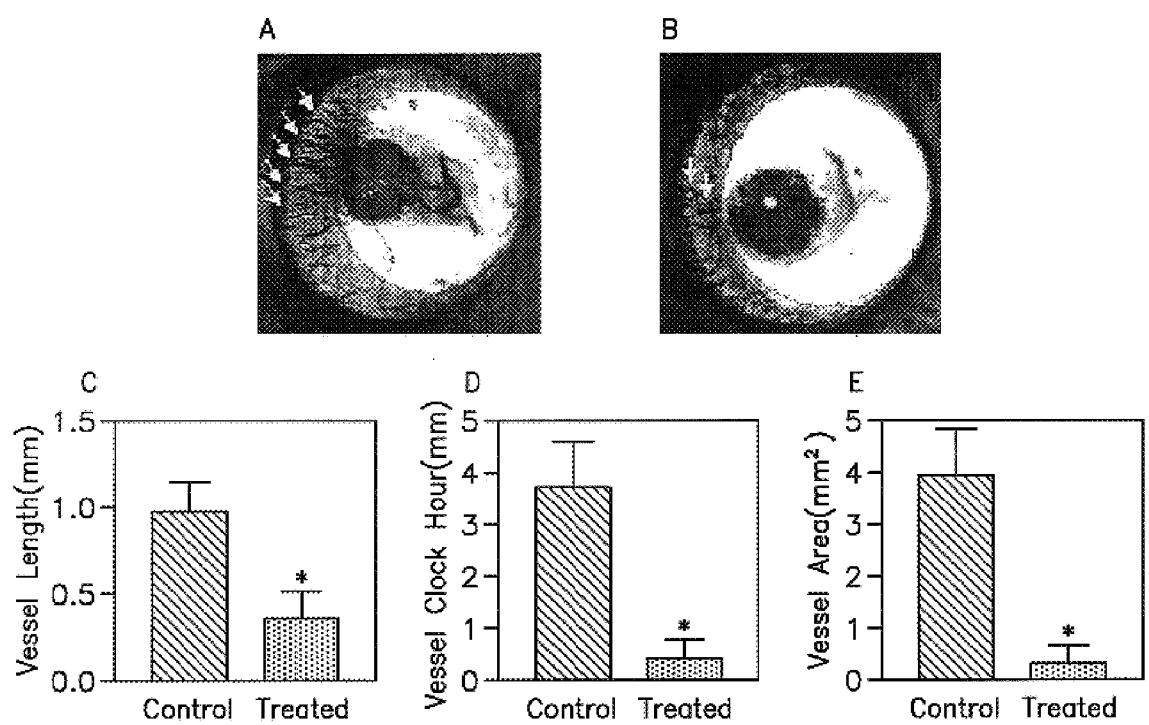
FIGS. 5(A) and 5(B) show inhibitory effect of arsenolite of the present invention on rat corneal neovascularization with oral administration.
FIGS. 5(D) and 5(E) are graphs showing vessel length, clock hour of neovascularization and vascular area of coreas of rat treated with oral administration of arsenolite of the present invention.

As shown in FIGS. 5A and 5B, systemic treatment of rat with arsenolite by oral administration at a concentration of 50 mg/kg/day for 7 days significantly inhibited bFGF-induced rat corneal neovascularization. Also, as shown in FIGS. 5C and 5D, the length and clock hours of corneal circumferential neovascularization were inhibited more than 60%. FIG. 5E confirms that the area of neovascularization in arsenolite-treated rats was suppressed by approximately 90%. The density of corneal vessels in the arsenolite-treated rats was also markedly reduced compared with that of control animals. The treated rats did not experience weight loss or unusual behavior over the course of the treatment, indicating that arsenolite was not toxic at the dose applied in the experiments.

Therefore, arsenolite of the present invention, solid $As_4O_6$, is a novel angiogenesis inhibitor that is sufficiently potent to suppress angiogenesis in vitro and in vivo. Also, arsenic compounds can be utilized for medication of varioius angiogenic diseases.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for treating diabetic retinitis without inducing apoptosis or cytotoxicity, comprising the step of administering to an animal suffering from diabetic retinitis 0.05–50 mg/kg weight of arsenolite (solid $As_4O_6$).

2. The method of claim 1 wherein the animal is human.

3. A method for treating arthritis without inducing apoptosis or cytotoxicity, comprising the step of administering to an animal suffering from arthritis 0.05–50 mg/kg weight of arsenolite (solid $As_4O_6$).

4. The method of claim 3 wherein the animal is human.

5. A method for treating hemangioma without inducing apoptosis or cytotoxicity, comprising the step of administering to an animal suffering from hemangioma 0.05–50 mg/kg weight of arsenolite (solid $As_4O_6$).

6. The method of claim 5 wherein the animal is human.

7. A method for treating psoriasis without inducing apoptosis or cytotoxicity, comprising The step of administering to an animal suffering from psoriasis 0.05–50 mg/kg weight of arsenolite (solid $As_4O_6$).

8. The method of claim 7 wherein the animal is human.

\* \* \* \* \*